(12) United States Patent
Martin

(10) Patent No.: US 7,285,246 B1
(45) Date of Patent: Oct. 23, 2007

(54) HAND-HELD FLUID ANALYZER

(75) Inventor: Lawrence Martin, St. Petersburg, FL (US)

(73) Assignee: Akers Acquisition Sub, Inc., Thorofare, NJ (US)

( * ) Notice: Subject to any disclaimer, the term of this patent is extended or adjusted under 35 U.S.C. 154(b) by 823 days.

(21) Appl. No.: 10/604,810

(22) Filed: Aug. 19, 2003

(51) Int. Cl.
*B32B 5/02* (2006.01)
*B32B 27/04* (2006.01)
*B32B 27/12* (2006.01)
*G01J 1/48* (2006.01)
*G01N 7/00* (2006.01)

(52) U.S. Cl. ............... 422/86; 422/50; 422/52; 422/55; 422/56; 422/57; 422/58; 422/68.1; 422/69; 422/82.05; 422/83; 422/84; 422/85; 422/88; 436/164; 436/165; 436/166; 436/167; 436/169; 436/174; 436/178; 436/181; 73/1.01; 73/1.02; 73/23.2; 73/23.3

(58) Field of Classification Search .............. 422/50, 422/52, 55, 56, 57, 58, 68.1, 69, 82.05, 83, 422/84, 85, 86, 88; 436/164, 165, 169, 174, 436/178, 181; 73/1.01, 1.02, 23.2, 23.3
See application file for complete search history.

(56) References Cited

U.S. PATENT DOCUMENTS

| | | | | |
|---|---|---|---|---|
| 3,022,141 A | * | 2/1962 | Grosskopf | 422/60 |
| 3,033,655 A | * | 5/1962 | Grosskopf | 422/86 |
| 3,100,692 A | * | 8/1963 | Wachter | 422/86 |
| 4,272,479 A | * | 6/1981 | Huneke et al. | 422/57 |
| 4,300,910 A | * | 11/1981 | Pannwitz | 436/102 |
| 4,329,153 A | * | 5/1982 | Leichnitz | 436/80 |
| 4,330,297 A | * | 5/1982 | Leichnitz | 436/84 |
| 4,740,475 A | | 4/1988 | Paul | |
| 4,928,887 A | * | 5/1990 | Miettaux | 239/584 |
| 5,079,141 A | * | 1/1992 | Niskanen et al. | 435/7.34 |
| 5,156,159 A | * | 10/1992 | Lampotang et al. | 600/532 |
| 5,313,959 A | * | 5/1994 | Monthony et al. | 600/572 |
| 5,432,094 A | * | 7/1995 | Delente | 436/127 |
| 5,552,324 A | * | 9/1996 | Liu | 436/132 |
| 5,750,184 A | * | 5/1998 | Imburgia | 427/2.13 |
| 5,830,344 A | * | 11/1998 | Priddy et al. | 205/775 |
| 5,834,626 A | * | 11/1998 | De Castro et al. | 73/23.3 |
| 6,942,835 B2 | * | 9/2005 | Monblanc et al. | 422/61 |

\* cited by examiner

*Primary Examiner*—Brian Sines
(74) *Attorney, Agent, or Firm*—Ronald E. Smith; Smith & Hopen, P.A.

(57) ABSTRACT

A hand-held device detects the presence of a preselected substance in the breath. A deformable housing forms a test chamber for interacting an indicator reagent with the breath. An ampoule positioned inside the housing is ruptured by manual pressure through the walls of the housing. The contents of the ruptured ampoule are exposed to the breath introduced into the chamber. The presence of a substance in the breath causes the indicator reagent to undergo a visually ascertainable change. The ampoule is secured within the housing by a pair of filter plugs having inboard concavities to receive the rounded ends of the ampoule to center it within the housing, and plural detents prevent slippage of the filters. Additional embodiments lower the user's risk of being cut by glass shards, prevent reagent inhalation, enhance the visual aspects of the device, and physically indicate the presence of breath flowing through the device.

34 Claims, 12 Drawing Sheets

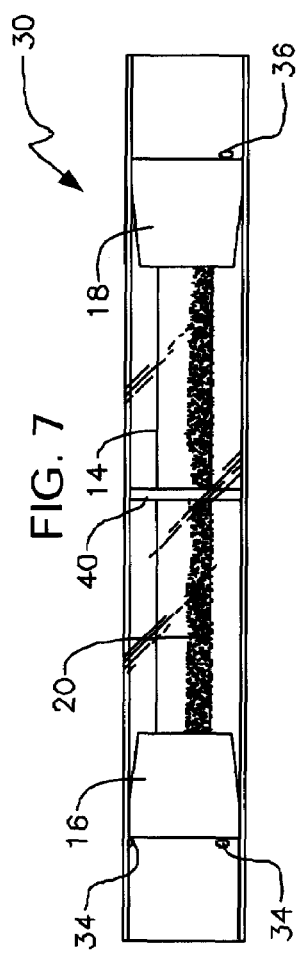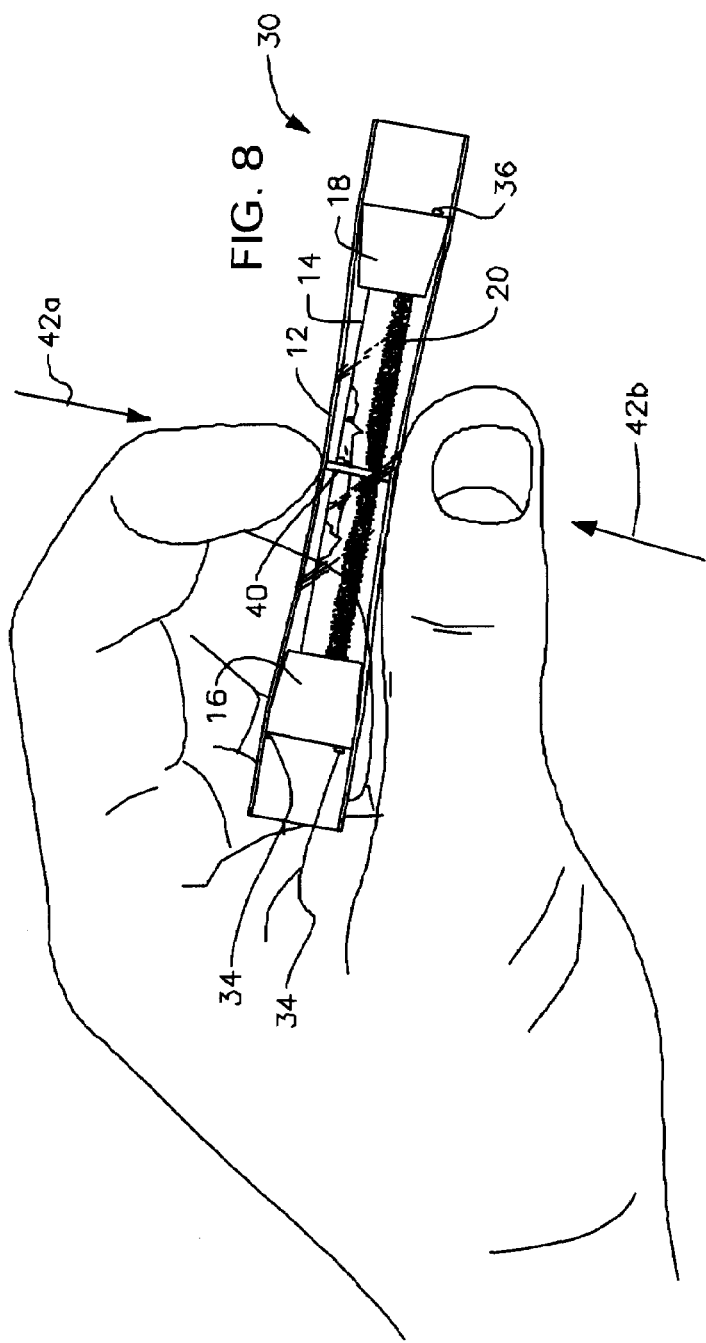

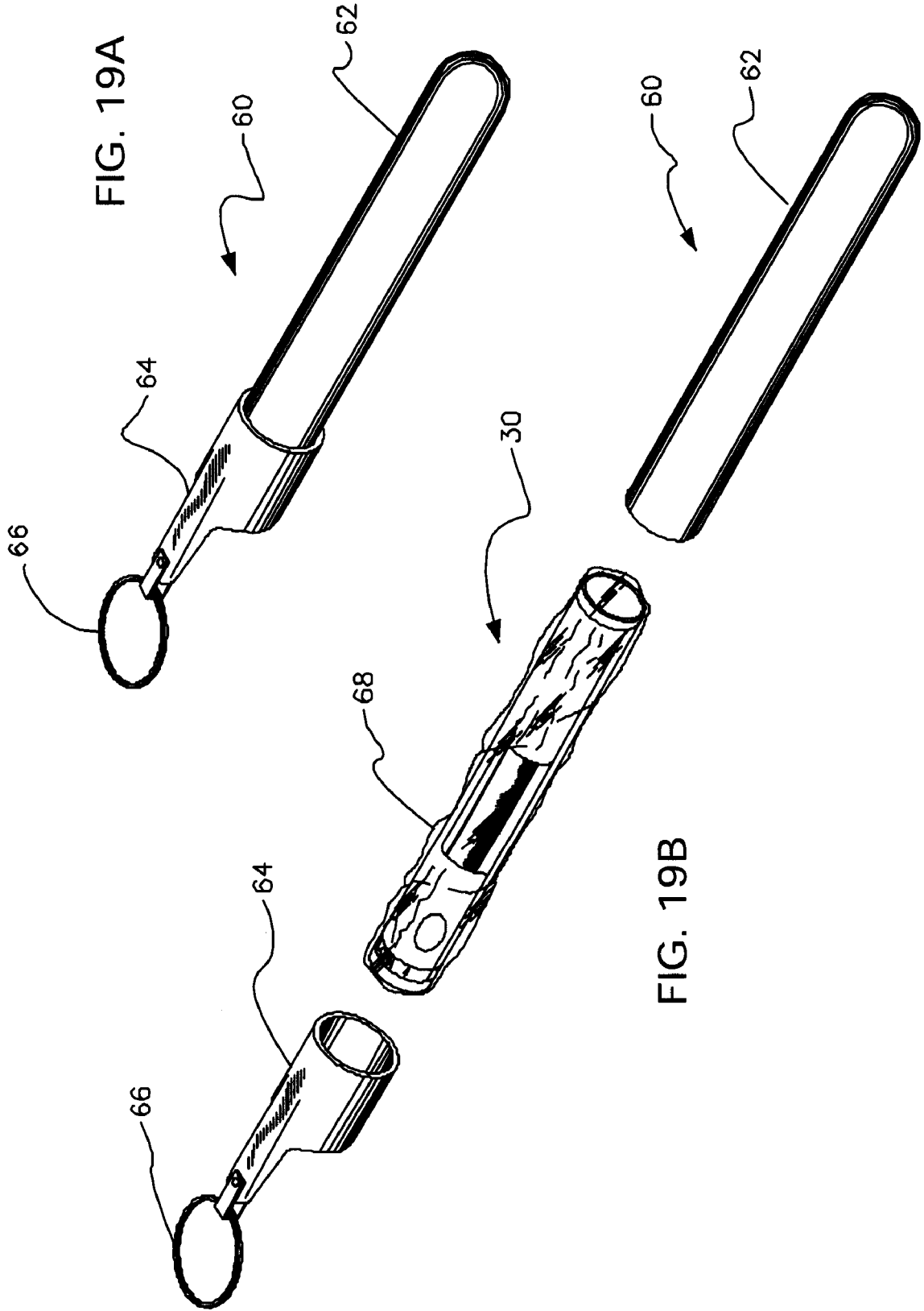

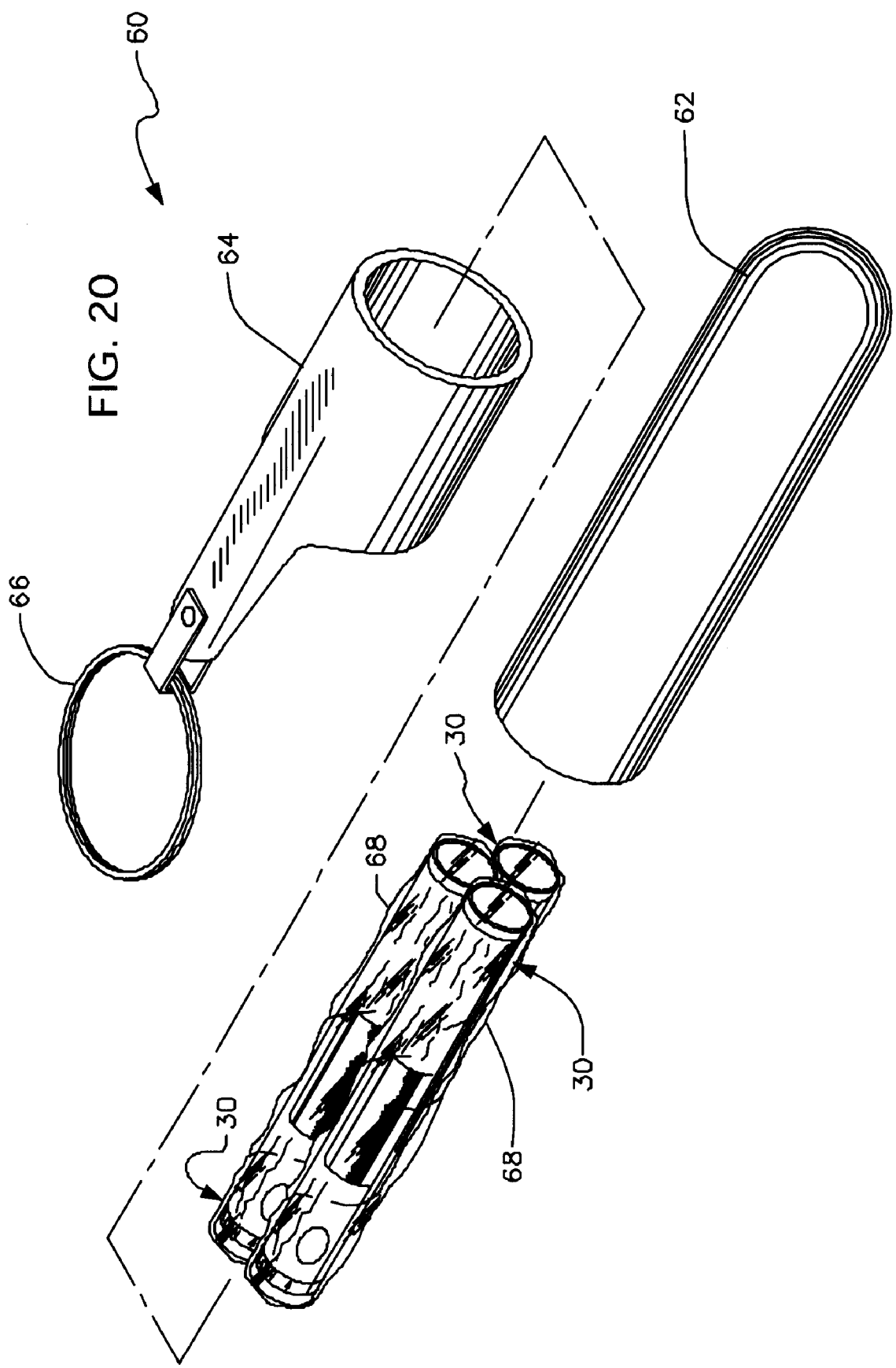

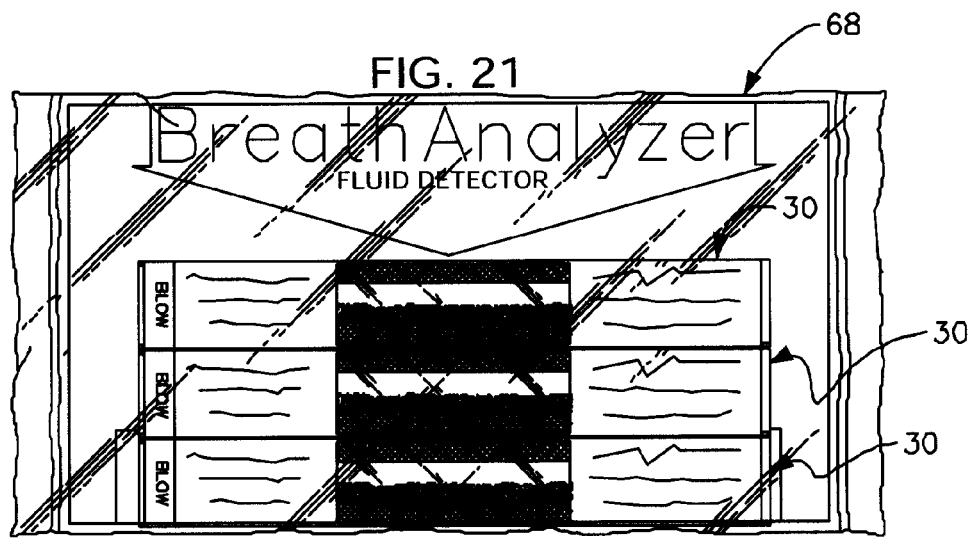
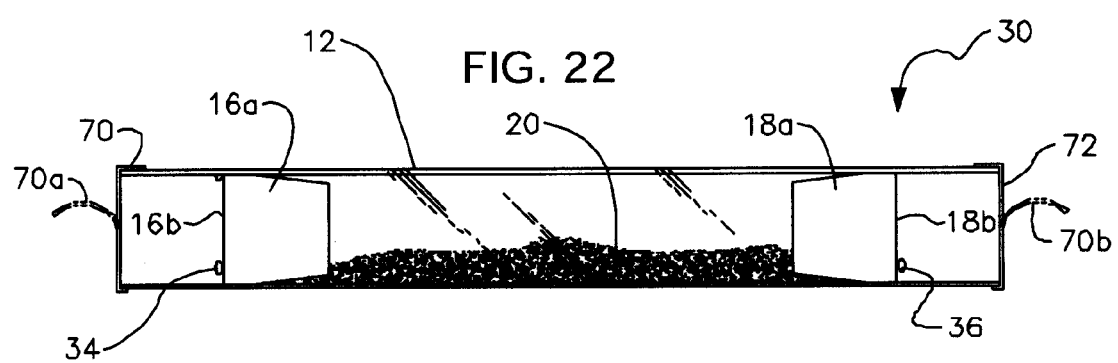

HAND-HELD FLUID ANALYZER

BACKGROUND OF INVENTION

1. Field of the Invention

This invention relates, generally, to disposable, field usable detectors for detecting the presence of substances in test fluids by use of indicator chemistry. More specifically, this invention relates to single-use, disposable devices for efficiently detecting the presence of controlled or other substances in the breath or other fluid by employing chemical indicators that react in a certain prescribed manner to the presence of such substance.

2. Description of the Prior Art

U.S. Pat. No. 4,740,475, awarded Apr. 26, 1988 to Paul, discloses an alcohol detection device that addresses the problem of "chemical indicator freshness." The indicator reagents typically used in these devices tend to deteriorate when exposed to air or moisture prior to use. Thus, the devices have to be handled and stored carefully. The reliability of these types of tests is questionable in the event of breakage or improper sealing.

However, the potential ease of use and reliability of low-cost, throw-away substance detectors using indicator reagent chemistry has continued to encourage researchers to develop a method of insuring the freshness and integrity of the indicator reagents to increase the accuracy and reliability of the tests. Various units and cartridges have been developed containing plugs and seals in an effort to assure indicator reagent freshness.

For example, the detector device shown in the Paul patent has a flexible, deformable housing that forms a test chamber for interacting an indicator reagent with the sample fluid. A rupturable ampoule containing an indicator reagent is positioned within the housing. The indicator reagent completely fills the ampoule and the diameter of the ampoule is only slightly less than the diameter of the lumen of the deformable housing.

Two porous plugs, located at opposing ends of the ampoule, maintain the position of the ampoule within the housing. To use the device, a user ruptures the glass ampoule through application of a predetermined pressure through the walls of the deformable housing. The user then blows through the opening at one end of the device, causing the breath to be exposed to the indicator reagent that has been introduced into the chamber by the breaking of the ampoule. In the presence of the predetermined substance in the sample fluid, the indicator reagent undergoes a known change in color.

The Paul device is characterized as being portable. However, the glass ampoule is easily broken if the device is carried in a pocket or other relatively unprotected container. Thus, the device is portable only when carefully transported.

There is almost no space between an outer housing of vinyl and the glass ampoule therewithin. Thus, the device is extremely fragile, easily broken, and thus is not truly portable. Moreover, the absence of space between the vinyl housing and the glass ampoule can result in cut fingers when the housing is squeezed to break the ampoule.

Thus there is a need for a truly portable detector having enhanced safety features.

Moreover, the ampoule is completely filled with the indicator reagent. This offers significant resistance to fluid flow. Thus, there is a need for an improved detector with less resistance to fluid flow so that a user need not blow as hard as when using the Paul device.

A considerable amount of force may be required to crush the Paul ampoule. A need exists, therefore, for a means that reduces the amount of force that a user must apply to the deformable housing to achieve rupturing of the ampoule.

Glass shards may cut through the vinyl housing and cut a user's finger or thumb when the ampoule is broken. Thus, there is a need for an improved detector structure that reduces the chances that a user will be cut when crushing the ampoule.

A user may also ingest or inhale indicator reagent by breathing inwardly instead of exhaling when using the Paul device. A need therefore exists for an improved detector structure that ensures that no user will be able to ingest or inhale the indicator reagent even if the detector is improperly used.

Visual inspection of the indicator reagent may fail to detect color changes in the indicator reagent because the Paul detector is made primarily of clear materials. The housing is typically formed of clear vinyl and the ampoule is formed of clear glass. Depending upon the amount of background clutter that exists in the ambient environment, a color change may be undetectable. There is a need, therefore, for a way to frame the indicator reagent to enhance the effectiveness of a visual inspection. It would also be advantageous if a way could be found to increase the contrast between the reagent indicator and the background against which the reagent indicator is viewed.

Some indicator reagents turn into a first color when a first concentration of the tested—for substance is present, a second color when a higher concentration is detected, a third color when a still higher concentration is detected, and so on. Thus there is a need for a label containing information about the meaning of the various colors where a detector is provided with such a reagent.

There is also a need for a detector that provides a physical marker indicating whether or not gaseous fluid is flowing through the lumen of the detector.

In view of the fragile nature of the Paul detector, there is also a need for a substance detector that is protected from easy breakage so that it is truly portable.

A need also exists for a detector having no ampoule therewithin to reduce the cost of manufacturing and also to enhance the safety of the detector by eliminating the glass shards that are produced upon rupturing of an ampoule.

However, in view of the prior art considered as a whole at the time the present invention was made, it would not have been obvious to those of ordinary skill in the pertinent art that the identified needs were in existence nor would it have been obvious how to fulfill such needs if they had been identified.

SUMMARY OF INVENTION

The long-standing but heretofore unfulfilled need for a truly portable, hand-held, disposable, field usable, lightweight device for detecting the presence of alcohol or other preselected substances in body fluids, particularly the breath, is now met by a new, useful, and nonobvious invention.

The novel detector includes a vinyl housing that is preferably generally cylindrical in shape and thus has a lumen that extends from a first open end thereof to a second open end thereof. A rupturable glass ampoule containing an indicator reagent is positioned in the lumen of the vinyl housing.

In a first embodiment, the diameter of the ampoule is less than the diameter of the lumen of the housing to provide a radial space therebetween for safety purposes. Moreover, the ampoule is only about half-filled with indicator reagent to reduce the resistance to fluid flow therethrough after the ampoule has been ruptured.

In the first embodiment, a pair of porous filter members flank the ampoule but no means are provided that prevent the reduced-diameter ampoule from tilting within the housing.

In a second embodiment, the reduced-diameter ampoule is secured within the vinyl housing from slipping out of its optimal position by an improved pair of porous filters, located on opposite ends of the housing, each of which has a concavity formed therein that accepts a corresponding rounded end of the ampoule. In this way, the reduced-diameter glass ampoule is suspended within the vinyl housing, spaced sufficiently away from the deformable walls of said vinyl housing so that inadvertent pressure applied to said vinyl housing does not rupture the ampoule.

In a third embodiment, at least one detent protrudes radially inwardly into the lumen of the deformable housing to prevent sliding displacement of the filters. A punch tool may be advantageously employed to create the detents.

In a fourth embodiment, a slightly compressible washer is positioned mid-length of the ampoule so that when the housing is manually compressed, the force of compression is concentrated by the narrow profile of the washer so that the ampoule breaks with less force than would be required in the absence of such concentration. The washer further spaces the digits of the user further from the glass shards created by the breaking of the ampoule.

In a fifth embodiment, the digits of the user are protected by the provision of a double-walled vinyl housing. This tube-in-tube design doubles the thickness of the walls of the housing, thereby providing an increased safety margin against the glass shards.

A sixth embodiment eschews the porous filters of the first five embodiments and provides hollow plugs having one-way flaps that open only in response to fluid flow in a predetermined direction. The flaps do not open if the user blows into the wrong end of the detector. Moreover, the flaps do not open if the user sucks on the correct end of the housing, thereby preventing ingestion or inhalation of the indicator reagent.

A unique label frames the indicator reagent in a seventh embodiment to enhance the ability of a user to see changes in color of said indicator reagent. The reverse side of the label is dark in color to further facilitate visual inspection of the indicator reagent by increasing the contrast between the indicator reagent and said dark background.

An eighth embodiment provides a label that indicates multiple color changes in the indicator reagent that correspond to multiple concentrations of tested substance so that a user may receive more detailed information than in those embodiments that test only for one threshold of the tested substance.

Any label may also be eliminated by printing the text and graphical material of the label directly onto the tube by screen printing or other suitable printing technique.

Streamers that indicate whether or not a user is blowing through the lumen of the detector are provided in a ninth embodiment. The streamers also indicate the length of time the user is exhaling through said lumen. One or more streamers may be provided and the streamers may take the form of strings, ribbons, tubes, or the like.

In a tenth embodiment, a flexible, inflatable bag is secured to the discharge end of the device in fluid communication with the lumen of the detector. Thus, the bag is inflated when a user blows through said lumen. A user, therefore, cannot pretend to blow through the lumen without being caught.

In an eleventh embodiment, the detector is made truly portable by being housed within a sturdy container that may be carried in a pocket or other suitable carrier without breakage. In a preferred version of the eleventh embodiment, the sturdy container is provided in the form of a hollow key ring fob having a first part for housing the detector and a second part that provides a closure means. A key ring is secured to the closure means so that it is a simple matter to remove the closure means to enable removal of the detector from the container.

A twelfth embodiment provides a container adapted to hold more than one detector.

A thirteenth embodiment eliminates the ampoule or ampoules employed in the other embodiments. Removable seals are secured to opposite ends of the housing to provide a hermetic seal so that the indicator reagent is not subjected to fluid flow until both seals are removed. The filters are employed as in the other embodiments to contain the indicator reagent therebetween.

A fourteenth embodiment adds a different indicator reagent to each filter of the thirteenth embodiment. This enables simultaneous detection of three different substances.

The novel detector may therefore be summarily described as a truly portable, disposable device for detecting the presence of a substance in a test fluid. The novel device includes a flexible and resilient, deformable first housing of generally cylindrical shape. An ampoule adapted to sealably retain therein an indicator reagent is positioned within the first housing and said ampoule has a diameter substantially less than the diameter of the first housing. The ampoule is adapted to be ruptured when subjected to a manually applied, radially inwardly directed force applied to said first housing.

In the first embodiment, as aforesaid, a first filter member is positioned within a lumen of the first housing in abutting relation to a first end of an ampoule, having a diameter substantially less than the diameter of the first housing, and a second filter member is positioned within the lumen of the first housing in abutting relation to a second end of the ampoule.

The ampoule has rounded opposite ends and is only about half-filled with indicator reagent so that a user need not exert extreme force when blowing through the detector.

In a second embodiment, a first concavity is formed in an inboard end of the first filter member and a second concavity is formed in an inboard end of the second filter member. The first concavity is complementary in size and shape to a convex first rounded end of the ampoule and the second concavity is complementary in size and shape to a convex second rounded end of the ampoule. The indicator reagent undergoes a visually detectible change in the presence of a predetermined amount of the substance. Moreover, the first and second concavities hold the ampoule in substantially coincident relation to a longitudinal axis of symmetry of the first housing.

Each filter has a first, outboard part of circular transverse cross-section so that it fits snugly within the lumen of the housing and a second, inboard part that is tapered downwardly to facilitate sliding introduction of the respective filters into opposite ends of the housing during assembly of the detector.

In a third embodiment, the detector further includes a first detent formed in the housing in outboard relation to the first filter member and a second detent formed in the housing in outboard relation to the second filter member. The first and second filters are constrained against longitudinal travel in an inboard direction by the ampoule and are constrained against longitudinal travel in an outboard direction by the first and second detents.

A fourth embodiment of the detector includes a compressible washer means having a central aperture. The compressible washer means is positioned about mid-length of the ampoule, and the ampoule is received within the central aperture. The compressible washer means has an outer periphery in substantial contact with an inner wall of the first housing. Accordingly, the manually applied radially inwardly directed force is applied to the compressible washer and causes compression of the central aperture and hence rupturing of the ampoule. The compressible washer provides a spacing between the first housing and the ampoule to reduce the chances that a glass shard from the ruptured ampoule will cut a finger or thumb of an individual applying said manual pressure.

A second flexible and resilient housing ensleeves the first housing in a fifth embodiment. The chance that glass shards, created by a ruptured ampoule in response to application of the manually applied radially-inwardly directed pressure against the first and second housings, will cut a finger or thumb of an individual applying manual pressure is reduced by the presence of the second housing.

In a sixth embodiment, a first hingedly mounted flap is formed in an outboard end of the first filter member. The first flap is adapted to admit fluid flow in one direction only. A second hingedly mounted flap is formed in an outboard end of the second filter member and the second flap is adapted to admit fluid flow in one direction only. Thus, a fluid may flow through the device in only one direction so that the indicator reagent cannot be inhaled.

A label has a first end that wraps completely around a first end of the housing and having a second end that wraps completely around a second end of the housing. The label also has a middle section that wraps partially around said housing to create a window in said middle section. The window enhances visual inspection of the indicator reagent. A dark color is printed on the reverse side of the label so that the color of the indicator reagent is clearly visible against said dark color.

The ampoule may be adapted to contain an indicator reagent that changes into a plurality of differing colors depending upon a percentage of the substance detected in the fluid. A label is secured to the housing and a first plurality of color codes is imprinted upon the label. Each color code indicates a percentage of substance present in the fluid. If the indicator reagent changes color in response to contact with the fluid, visual inspection of the plurality of color codes indicates the percentage of the substance detected in the fluid.

In the alternative, a label-less embodiment may be provided where a color code or color codes may be imprinted directly on the vinyl housing by a suitable printing method. The color code or codes may take the form of a box or boxes of differing colors, or a colored line or lines that partially or fully circumscribe the housing, and so on. As another example, the entire housing could be imprinted so that it has the color that the indicator reagent will change to upon detecting a substance. Where the indicator reagent may change into two different colors upon detection of differing levels of a detected substance, a first half of the housing could be imprinted with the first color and a second half of the housing could be imprinted with the second color, and so on for additional color changes.

An elongate, flexible streamer in the form of one or more strings, ribbons, tubes, or the like, or combinations thereof, is secured to a discharge end of the housing. The streamer is mounted so that it is in fluid communication with fluid flowing through a lumen of the housing. The streamer remains substantially in a position of repose if fluid is not flowing through the housing and the streamer is displaced from the position of repose when fluid is flowing through the lumen. An amount of time that fluid flows through the lumen may therefore be measured by measuring the amount of time the streamer is displaced from the position of repose.

A flexible, inflatable bag may be secured to the discharge end of the detector, in lieu of the streamer. The bag inflates when a user properly blows through the lumen of the detector and fails to inflate if a user merely pretends to blow through the lumen.

The novel detector is housed in a substantially uncrushable or unbreakable container so that it may be carried in a pocket or other relatively unprotected carrying means without fear of breakage. In a preferred embodiment, the container is attached to a key ring and thus serves as a key fob.

The container may be sized to hold one or more detectors. It may be coated with glow-in-the-dark materials or otherwise treated to make it easy to see in low light conditions.

The ampoule or ampoules that hold the indicator reagent may be eliminated in yet another embodiment. Impregnating or coating the filters with differing indicator reagents may also be employed to enable simultaneous detection of multiple substances.

An important object of the invention is to provide disposable devices for efficiently detecting the presence of a particular substance in human fluids employing chemical indicators that react in a certain prescribed manner in the presence of the substance being tested for.

A more specific object is to provide a unique substance detection device for mobile testing of human breath that is safe, efficient, and effective.

Moreover, it is an important object of this invention to provide a detector having an ampoule that is spaced apart from the housing of the detector for safety purposes.

Another object is to provide an ampoule having less resistance to fluid flow than the ampoules of the prior art.

It is also an important object to provide a means for holding an ampoule of a substance detector in an optimal orientation so that the indicator reagent therewithin is evenly distributed therewithin, thereby increasing the reliability of the detector.

A closely related object is to provide such ampoule holding means so that the ampoule is not subject to unintentional breaking of the type that can occur when the ampoule is disposed in oblique relation to a longitudinal axis of the ampoule housing.

Another important object is to provide a means that prevents such ampoule from slipping within the lumen of the housing.

Another object is to provide a means for reducing the amount of force required to crush an ampoule while increasing the safety of the crushing operation.

Still another object is to provide a housing structure that provides an extra level of protection between a user's finger and thumb and glass shards created by crushing the ampoule.

Yet another object is to provide a detector that does not operate unless a user blows through an indicated end thereof.

Another object is to provide a means that prevents a user from inhaling or ingesting an indicator reagent.

Another object is to provide a unique label that frames the indicator reagent, thereby enhancing the ability of a user to visually detect changes in reagent color.

Another object is to provide a color contrast surface behind the indicator reagent to further facilitate visual observation of color changes in said indicator reagent.

A further object is to provide a label that indicates multiple levels of the presence of the substance for which the test is made.

Another object is to provide a label-less housing where all information that could be imprinted upon a label is imprinted directly onto the housing.

A still further object is to provide a means for determining whether or not a user is exhaling through the lumen of the housing, and how long such exhalation is maintained.

Another object is to provide a container for the detector so that the detector is truly portable.

Still another object is to provide a detector having no ampoule therewithin.

Yet another object is to provide a no-ampoule detector where the filters are treated with differing indicator reagents to enable simultaneous detection of multiple substances.

The invention accordingly comprises the features of construction, combination of elements, and arrangement of parts as set forth in the detailed description that follows, and the scope of the invention will be indicated in the claims.

BRIEF DESCRIPTION OF DRAWINGS

For a further understanding of the nature and objects of the invention, reference should be made to the following detailed description, taken in connection with the accompanying drawings in which:

FIG. 7 is a side elevational view of the third embodiment when in repose;

FIG. 8 is a perspective view depicting the third embodiment when crushed;

FIG. 19A is a perspective view of the assembled novel protective container that houses the detector so that the detector is truly portable;

FIG. 19B is an exploded perspective view depicting the protective container, its closure means, and the novel detector;

FIG. 20 is an exploded perspective view depicting a container adapted to hold more than one detector;

FIG. 21 is an elevational view depicting a plurality of detectors in a flat polybag; and FIG. 22 is an elevational view of an embodiment having no filter members.

Similar or identical reference numerals are used throughout the drawings to indicate similar or identical parts that are common to the several embodiments of the invention.

DETAILED DESCRIPTION

Figure 1A:
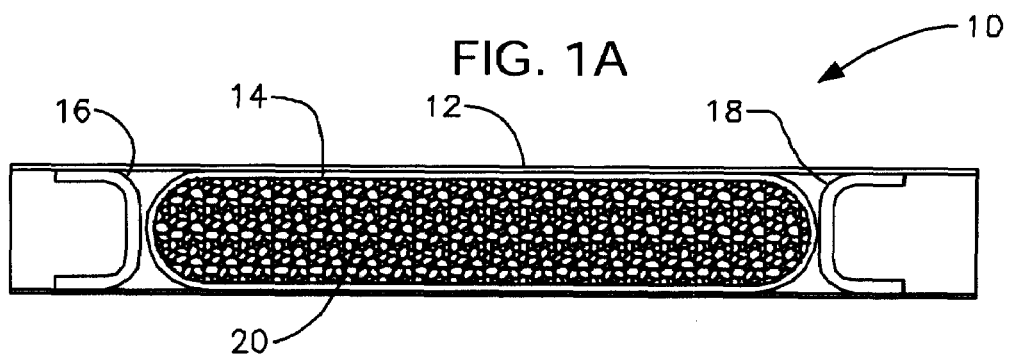
FIG. 1A is a side elevational view of the prior art device disclosed in the Paul patent, indicating the absence of space between the vinyl housing and the glass ampoule therewithin.

Referring now to FIG. 1A, it will there be seen that a detector of the prior art, disclosed in the above-identified patent to Paul, is denoted as a whole by the reference numeral 10. Note that there is no space between deformable housing 12 of vinyl construction and glass ampoule 14. Thus, when glass ampoule 14 is crushed by squeezing vinyl housing 12, the fingers employed in the crushing operation may be cut by glass shards generated by such crushing because the glass shards easily cut through vinyl housing 12.

Figure 1B:
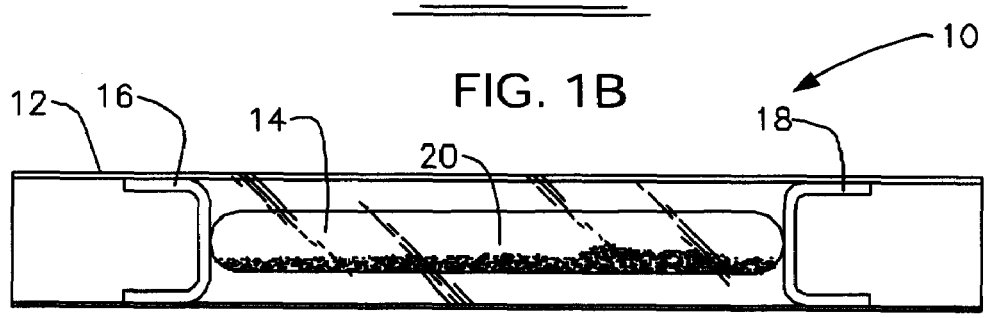
FIG. 1B is a side elevational view of a first illustrative embodiment of this invention where the diameter of the ampoule has been reduced.

FIG. 1B depicts the first embodiment of this invention. The diameter of glass ampoule 14 is reduced so that space is provided between vinyl housing 12 and glass ampoule 14. Thus, there is an increased measure of protection from glass shards, as compared to the patented embodiment of FIG. 1A. Moreover, ampoule 14, in the improved embodiment of FIG. 1B, is no longer completely filled. Instead it is about half full to make it easier to blow through detector 10 when ampoule 14 has been broken.

Figure 1C:
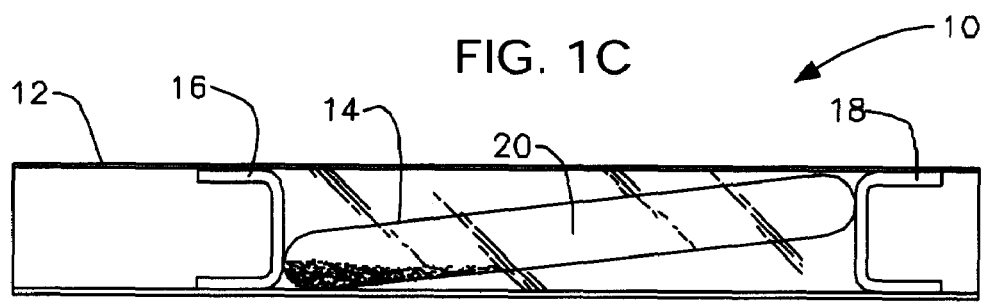
FIG. 1C is a side elevational view like that of FIG. 1B but where the filters at the opposite ends of the ampoule have slipped from their initial positions, resulting in canting of the improved ampoule.

However, as indicated in FIG. 1C, one or both of the filters at the opposite ends of the reduced-diameter ampoule of FIG. 1B may slip from their initial positions, allowing ampoule 14 to become tilted, or canted, within the substance detector housing. When this occurs, the tilt of the ampoule causes the chemical grains therewithin to tend to accumulate toward one end of the ampoule. If the accumulation becomes excessive, it can alter the effectiveness of the indicator.

Moreover, when ampoule 14 is oblique to a longitudinal axis of the housing, it becomes subject to unintentional, premature breakage because its ends may abut the housing and be easily ruptured even if relatively light, inadvertent pressure is applied to the housing.

The deformable character of housing 12 presupposes some elasticity so that housing 12 returns substantially to its original cylindrical shape after a user squeezes it to break glass ampoule 14, i.e., housing 12 is flexible and resilient. Accordingly, sufficient volume is provided to form the test chamber. However, the entire housing need not be deformable. Only that portion of housing 12 proximate to ampoule 14 need have sufficient deformability to transmit pressure to ampoule 14.

Even though the amount of indicator reagent 20 encapsulated within ampoule 14 is reduced by about half in this invention, visa vis the amount of indicator reagent used in the prior art, the amount is still effective. The amount of indicator reagent within ampoule 14 is calculated to suit the internal capacity of the test chamber and the amount of body fluid, whether liquid or gaseous, to be introduced into the lumen of detector 10.

Ampoule 14 is preferably positioned in the center of housing 12 in equidistantly spaced relation from the opposite ends of said housing. However, in FIG. 1C, filters 16, 18 have slipped from their respective optimal positions as aforesaid. Accordingly, ampoule 14 is not centered with respect to said housing.

Note further that housing 12 and ampoule 14 are both of clear, transparent construction. Thus, there is no means for framing indicator reagent 20 to facilitate visual inspection thereof. Nor is there any means for increasing the contrast between the indicator reagent and its background.

The ideal deployment of indicator reagent 20 includes no accumulations, i.e., the indicator reagent should be spread evenly between the opposite ends of ampoule 14. Any variance between ideal deployment and actual deployment introduces errors into the detection function performed by detector 10.

The patented version of the Paul detector (FIG. 1A) solves the canting problem by sizing the ampoule to have an outer diameter substantially equal to the inner diameter of the vinyl housing. Although such sizing prevents canting of the ampoule, it increases the chances that the fingers or thumb of a user will be cut at the moment the ampoule is crushed, as mentioned earlier.

Figure 2:
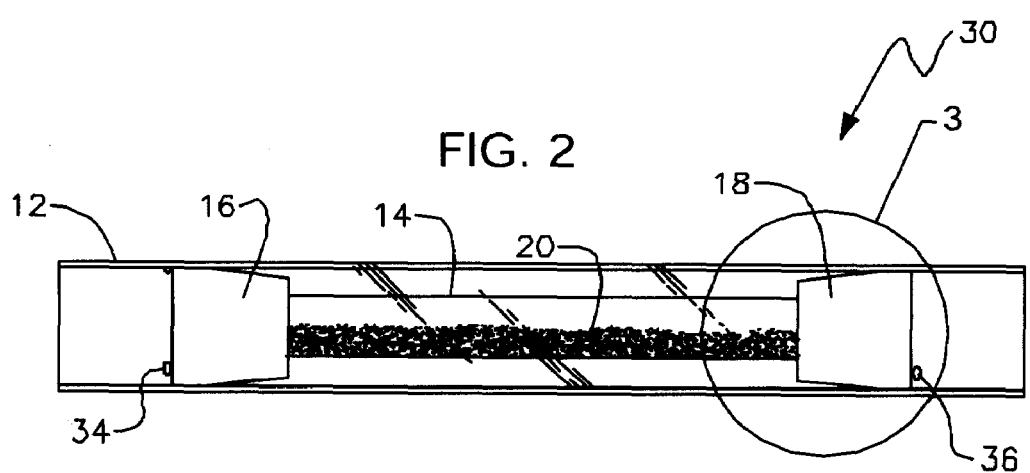
FIG. 2 is a side elevational view of a second embodiment of the present invention, depicting an untilted ampoule of the present invention disposed in centered relation with respect to the deformable housing.

The canted-ampoule problem is resolved by the second embodiment of this invention, denoted as a whole by the reference numeral 30 in FIG. 2. The longitudinal axis of symmetry of ampoule 14 is coincident with a longitudinal axis of symmetry of housing 12, with the result that indicator reagent 20 is evenly distributed within ampoule 14, even though the amount of said indicator reagent is only about half of the amount used in prior art detector 10 of FIG. 1A.

Figure 3:
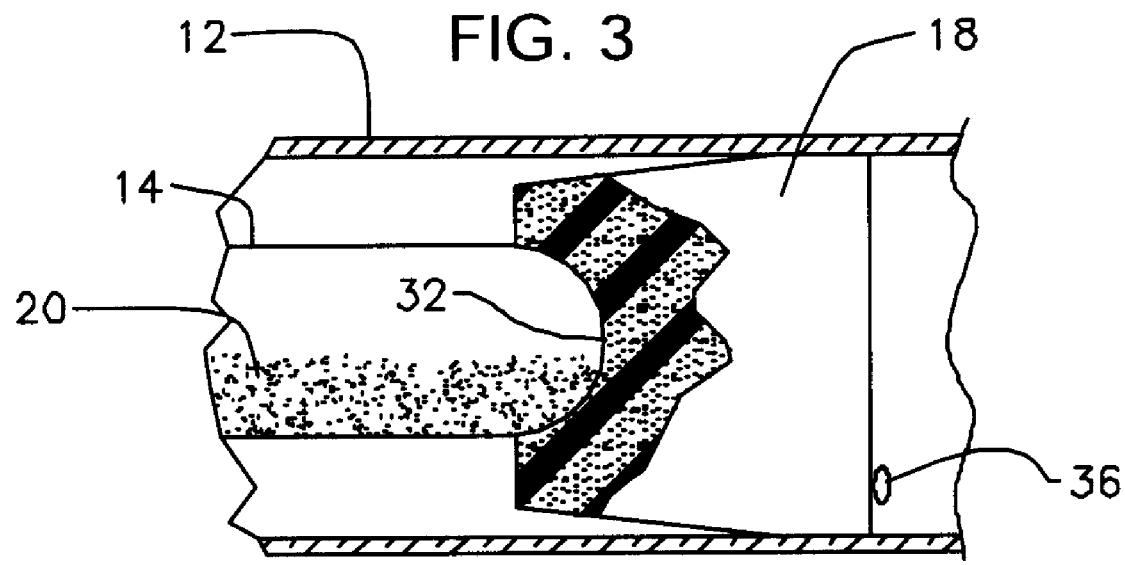
FIG. 3 is an enlarged, partially sectional view of the circled area denoted 3 in FIG. 2.

Centering of ampoule 14 as depicted in FIG. 2 is accomplished by forming concavity 32 in the inboard end of each filter 16, 18. FIG. 3 depicts concavity 32 formed in filter 18; the concavity formed in filter 16 has the same construction. As indicated in FIG. 3, the radius of curvature of each concavity is equal and complementary to the radius of curvature of the rounded ends of ampoule 14 so that the ends of said ampoule are perfectly seated within their respective concavities in stable, non-shifting relationship therewith. This structure maintains ampoule 14 in floating or suspended relation to the cylindrical walls of housing 12.

Each filter 16, 18 is formed of a firm but resilient porous material. Note that the inboard end of each filter 16, 18 has a diameter-reducing taper formed therein. More particularly, the respective outboard ends of each filter 16, 18 are circular in transverse cross section to ensure a snug fit with the lumen of tubular housing 12. The respective inboard ends are downwardly tapered to facilitate sliding introduction of the filters into the opposite ends of said housing.

In addition to providing an even distribution of indicator reagent 20, the filters having concave inboard faces also solve the problem of breakage associated with a canted ampoule of the prior art. The spacing between housing 12 and ampoule 14 is sufficient to avoid unintentional breakage of the latter when the former is slightly compressed in a radially inwardly direction.

However, the concavities do not solve the problem associated with unwanted longitudinal displacement of the filters of the type depicted in FIG. 1. The solution to that problem is embodied in the third embodiment of the invention which is also depicted in FIG. 2. At least one radially inwardly projecting protrusion 34 is formed in deformable housing 12 in outboard relation to filter 16 and at least one radially inwardly projecting protrusion 36 is formed in deformable housing 12 in outboard relation to filter 18. Each protrusion 34, 36 provides a detent means that prevents sliding of said filters away from ampoule 14. Thus, ampoule 14 prevents travel of the filters in an inboard direction and detents 34, 36 prevent travel of the filters in an outboard direction.

Figure 4:
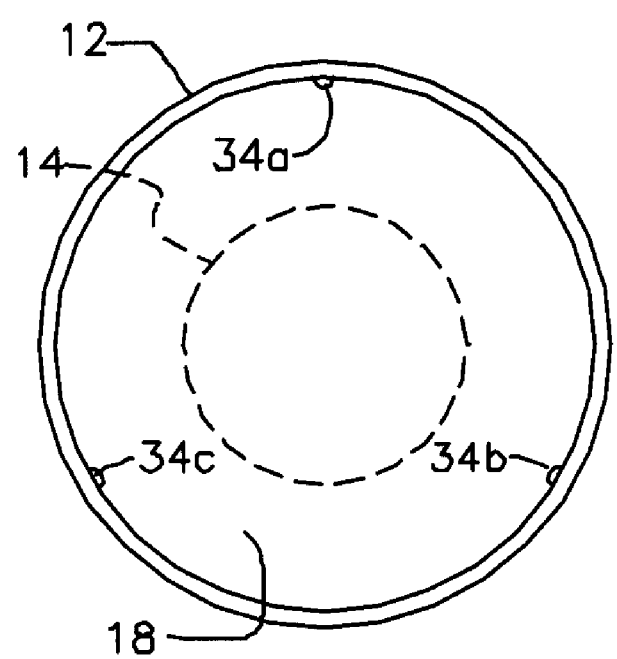
FIG. 4 is an end view of the embodiment of FIG. 2.

As depicted in FIG. 4, multiple protrusions may be formed in said deformable housing 12. In the example of FIG. 4, three protrusions 34a, 34b, and 34c are disposed in equidistantly and circumferentially spaced apart relation to one another. Protrusions 34a, 34b, 34c collectively provide detent 36.

By preventing longitudinal slipping of filters 16, 18, ampoule 14 is maintained in centered relation to housing 12 at all times.

Figure 5:
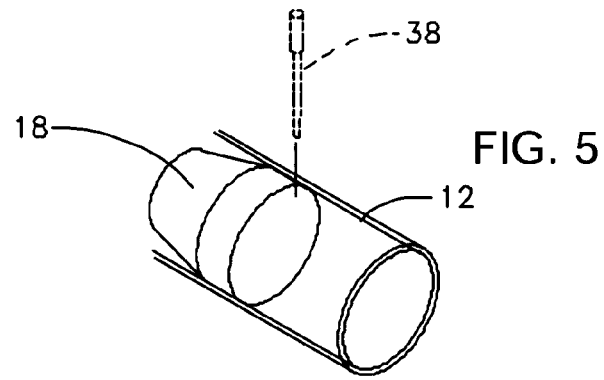
FIG. 5 is a perspective view depicting a tool, in phantom lines, employed to form detents in the deformable housing of this invention.

Detent 36 may be formed by any suitable means. FIG. 5 depicts a punch tool 38 in phantom lines, but other means for forming such detent are within the scope of this invention.

Figure 6:
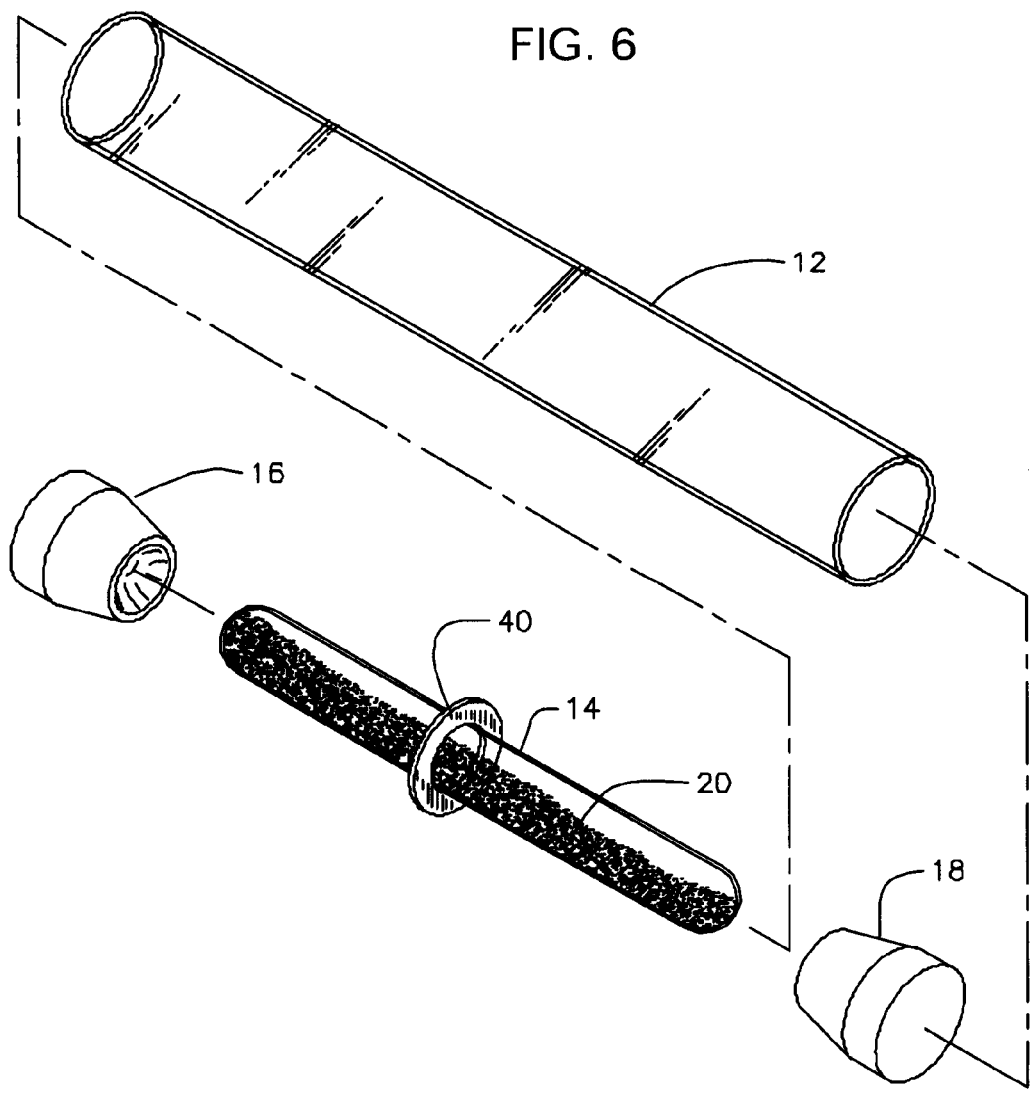
FIG. 6 is an assembly diagram depicting a third illustrative embodiment.

A fourth embodiment of the invention is depicted in FIGS. 6-8. In those Figs., a washer 40 is positioned substantially mid-length of ampoule 14. Washer 40 is formed of a firm but deformable material so that when radially-inwardly directed forces are applied to washer 40, said washer is compressed. More particularly, the diameter of the central aperture of said washer is compressed in response to such forces. Thus, as best understood by comparing FIGS. 7 and 8, depicting the in-repose and the squeezed conditions of housing 12, respectively, a manual application of converging forces, indicated by single-headed directional arrows 42a, 42b in FIG. 8, causes the diameter of the central aperture of the washer to decrease and to break glass ampoule 14.

Because washer 40 has a narrow profile, its central aperture, when compressed, applies a highly concentrated force against said ampoule 14. Therefore, less power is required to break ampoule 14 when said washer is provided.

Moreover, as is clear from FIGS. 7 and 8, washer 40 also provides the service of spacing the user's finger and thumb further from the broken pieces of glass that are created when ampoule 14 is crushed. Such spacing reduces the likelihood of an injury.

Ampoule 14 may also be scored or otherwise weakened at a preferred rupture point.

Figure 9:
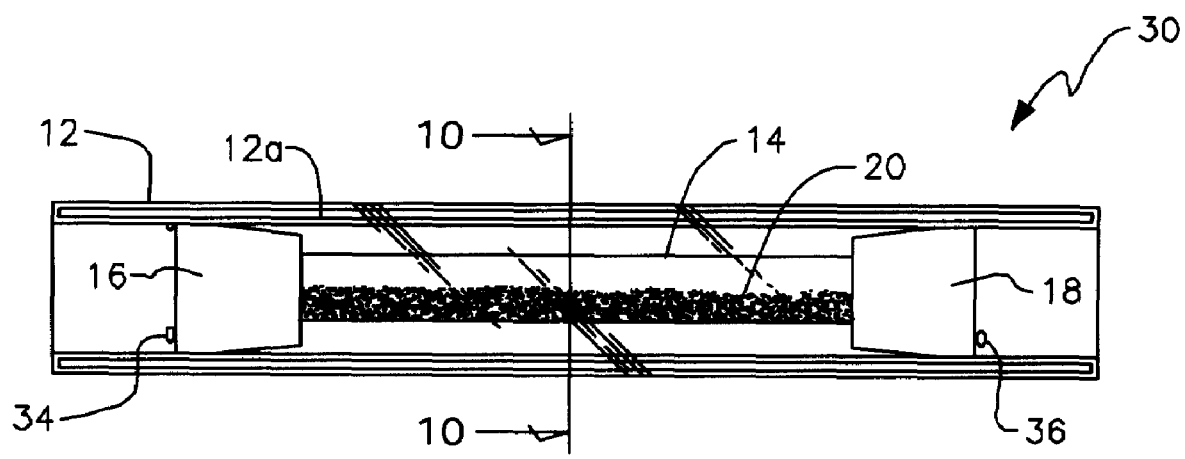
FIG. 9 is a side elevational view of a fourth embodiment.
Figure 10:
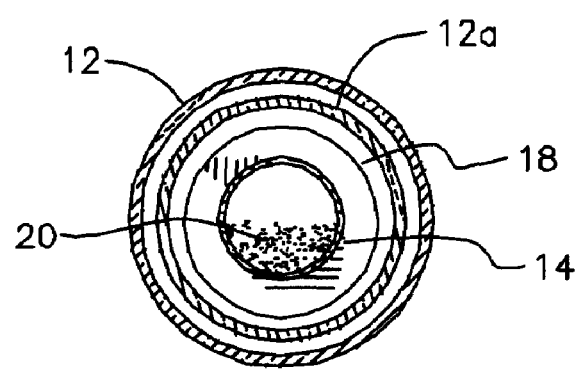
FIG. 10 is a transverse sectional view taken along line 10-10 in FIG. 9.

A second means for reducing the chances of such an injury is included in the fifth embodiment, depicted in FIGS. 9 and 10. In this embodiment, housing 12 is double-walled, i.e., a second housing, denoted 12a, is disposed within original housing 12, in a tube-in-tube structure. Accordingly, the amount of material, such as vinyl, disposed between the glass shards and the user's digits is doubled. This double shielding provides an enhanced safety factor.

Figure 11:
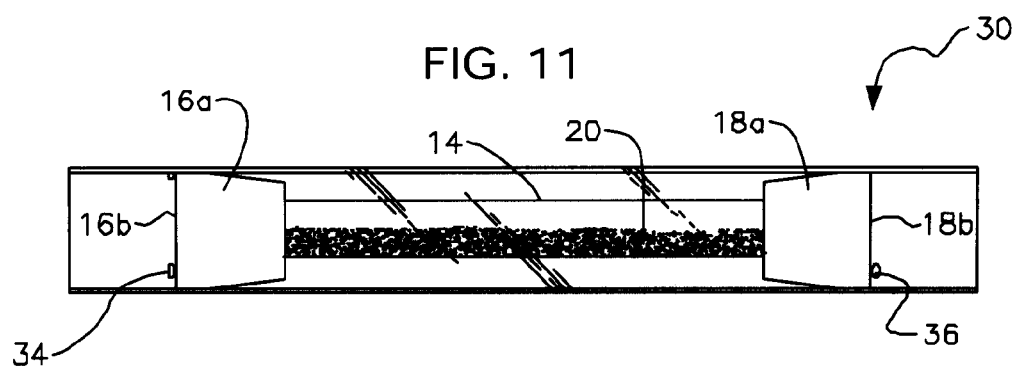
FIG. 11 is a side elevational view depicting the novel filter flaps when in repose.
Figure 12:
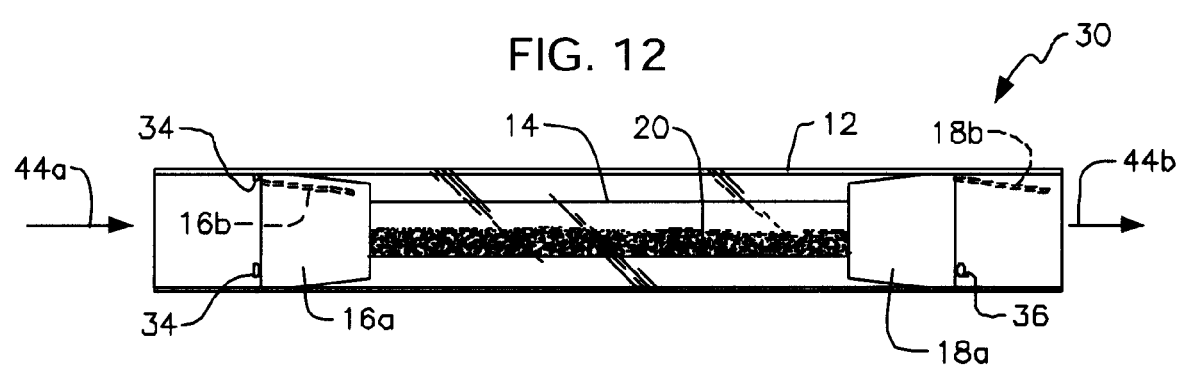
FIG. 12 is a side elevational view depicting the novel filter flaps when said filter flaps have been displaced from their respective positions of repose.
Figure 13:
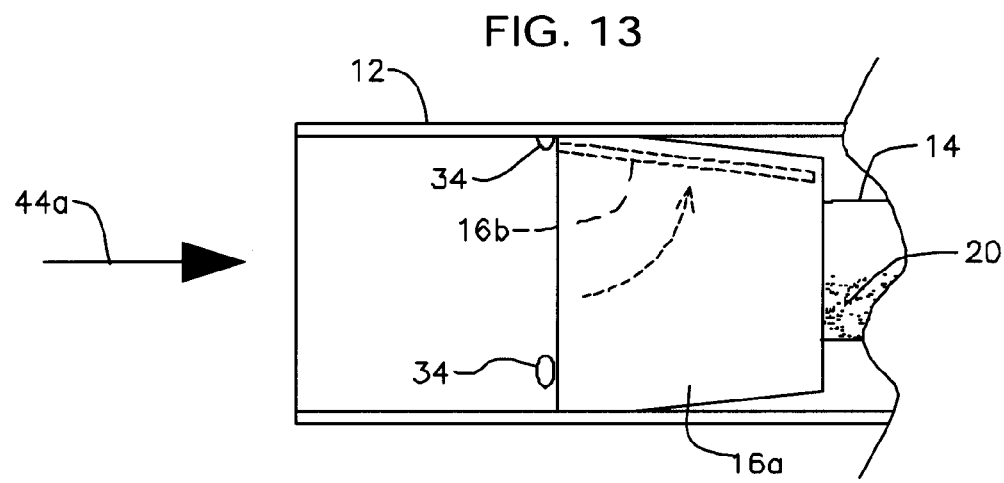
FIG. 13 is an enlarged, detailed view of one of the filter flaps when displaced from its position of repose.

Porous filters 16, 18 are eliminated in the sixth embodiment. As depicted in FIGS. 11-13, end pieces 16*a*, 18*a* are not formed of a porous material. Instead, hinged flap 16*b* is mounted at the leading end of end piece 16*a* and hinged flap 18*b* is mounted to the trailing end of end piece 18*a*. Flaps 16*b*, 18*b* are in repose in FIG. 11 because no gaseous or liquid fluid is flowing through housing 12. In FIG. 12, said flaps 16*b*, 18*b* are displaced by a fluid flow indicated by single-headed directional arrows 44*a*, 44*b*. The hinges may be living hinges or other suitable hinge means.

A more detailed view of flap 16*b* is provided in FIG. 13. It should be understood that neither flap 16*b*, 18*b* will open if a user blows into housing 12 in a direction opposite to the direction indicated by directional arrows 44*a*, 44*b*. In a commercial embodiment of the invention, one or more directional arrows 46 (see FIGS. 14-16A) indicating the required directional flow of the user's breath will be provided. The term "blow" (see FIGS. 14, 15, and 17A, 17B) may also accompany said directional arrows for emphasis or redundancy. Thus, a person too inebriated to blow into the correct end of detector 30 will automatically fail the sobriety test provided by said detector.

Figure 14:
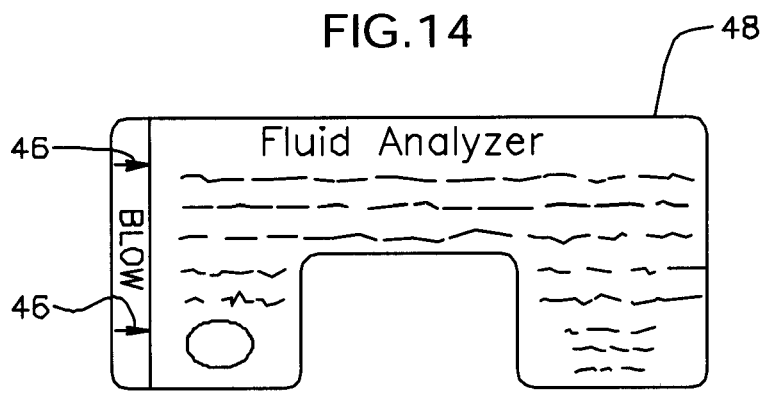
FIG. 14 is a front elevational view of a first embodiment of the novel label structure.
Figure 15:
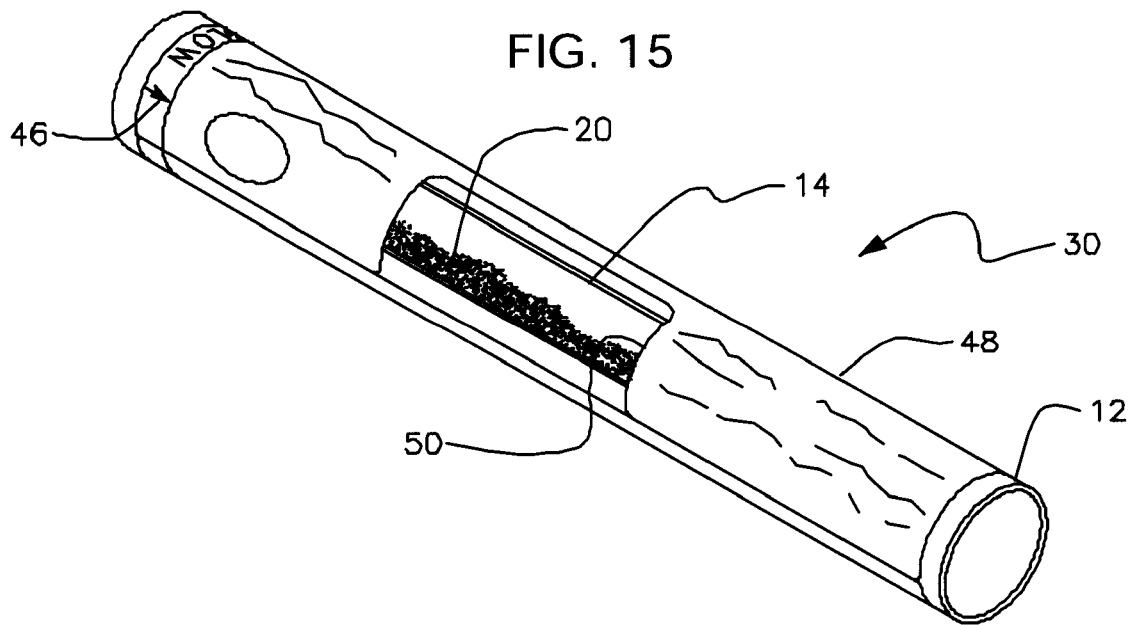
FIG. 15 is a view depicting the first embodiment of the novel label in its functional position.

The seventh embodiment of this invention provides a window for enhancing the viewing of indicator reagent 20. Label 48, depicted in its flat, front configuration in FIG. 14, is wrapped around housing 12 in the manner depicted in FIG. 15 to create a physical window 50 that enhances the ability of a user to visually detect changes in indicator reagent 20. Window 50 provides a frame that isolates indicator reagent 20 in a way not provided in the prior art design.

In a variation of this embodiment, the text or graphic materials appearing on the front surface of label 48 is imprinted directly onto housing 12 by screen printing or other suitable printing method. Lines printed on housing 12 could perform the function of demarcating a viewing window.

Some indicator reagents turn a first color when a first concentration of a substance is detected, a second color when a higher concentration is detected, and so on. The eighth embodiment of this invention thus provides color-coded label 52 of FIG. 16A. Box 52*a* has a first predetermined color and may be labeled "0.04%." Box 52*b* has a second predetermined color and may be labeled "0.08%." Box 52*c* has a third predetermined color and may be labeled "0.10%." In this way, a user may match the color of the indicator reagent after use with the color of one of said boxes and thus learn the alcohol (or other substance) content of the breath or other bodily fluid. Any number of boxes and corresponding concentration percentages may be provided, as long as each box has a specific and unique color and matches the color to which the reagent changes when exposed to alcohol or other substance of sufficient concentration to cause the indicator reagent to change to the corresponding color.

Figure 16A:
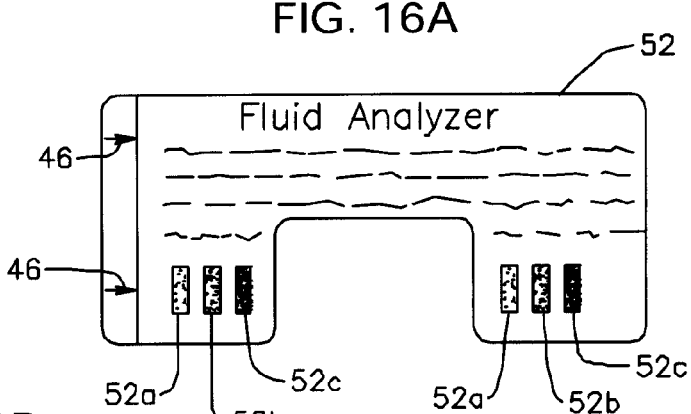
FIG. 16A is a front elevational view of a second embodiment of the novel label structure.
Figure 16B:
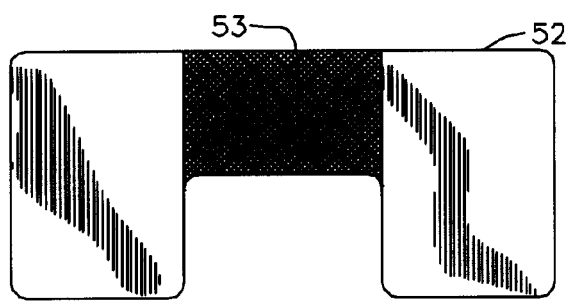
FIG. 16B is a rear elevational view of said second embodiment of the novel label structure.

FIG. 16B depicts the reverse side of label 52. Note that middle section 53 thereof is printed black, dark blue, or some other preselected color that sharply contrasts with indicator reagent 20 both before and after said indicator reagent has changed color.

Figure 17A:
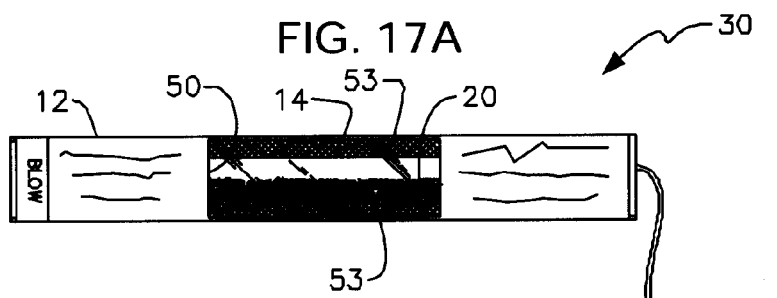
FIG. 17A is a side elevational view depicting the novel flow-detecting streamer in repose.
Figure 17B:
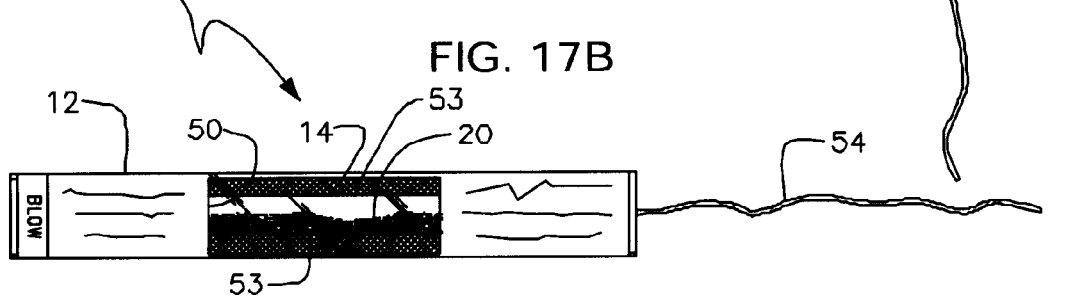
FIG. 17B is a side elevational view depicting the novel flow-detecting streamer in motion.

FIGS. 17A and 17B illustrate how dark middle section 53 provides an enhanced background contrast to further facilitate visual inspection of the indicator reagent after it has undergone one or more color changes.

In a variation of this embodiment, the entire front surface of label 52 may be printed in the color to which indicator reagent 20 changes when a preselected level of substance is detected. In another variation, where two levels of substance may be indicated, the left half of label 52 could be printed in the color that indicates a first level of substance has been detected and the right half of the label could be printed in the color that indicates a second level of substance has been detected. Where a reagent capable of changing into three different colors, depending upon the amount of substance detected, the left third of the label could be printed in a first color indicating detection of a first level of substance. The middle of the label (the part including window 50) could be printed in a second color indicating detection of a second level of substance, and the right third of the label could be printed in a third color indicating detection of a third level of substance, and so on for detectors that can change colors four or more times in response to detection of different levels of detected substances.

Labels 48 and 52 could also be obviated and the textual and graphic materials thereon imprinted directly to housing 12, as in the preceding embodiment. Housing 12 could be imprinted with a first color to which the indicator reagent changes upon detection of a target substance, with two colors if the indicator reagent responds to differing levels of detected substance by changing colors twice, and so on.

The eighth embodiment, depicted in FIGS. 17A and 17B, provides a light-in-weight streamer 54, or possibly a plurality of such streamers, secured to the exit end of housing 12. Each streamer 54 may take the form of a flexible string, ribbon, tube, or other suitable structure, or combinations thereof. The streamers defeat the intentions of a user who tries to blow past housing 12 and not through its lumen because said streamers deploy into the FIG. 17B position only when air passes through said lumen of said housing. The streamer or streamers also facilitate measurement of the length of time that the user has exhaled through said lumen. The length of exhalation is important because an exhalation that does not last a sufficient time will fail to cause indicator reagent 20 to change color. The amount of time for a reagent to change color if the tested substance is present is typically a few seconds.

Figure 18A:
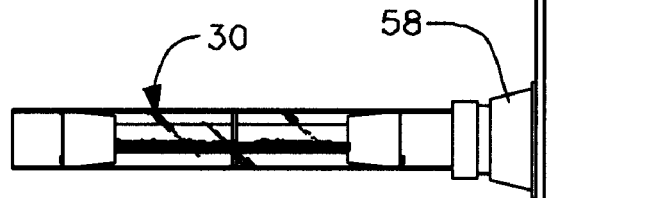
FIG. 18A is a side elevational view depicting the novel flexible, inflatable bag in repose.
Figure 18B:
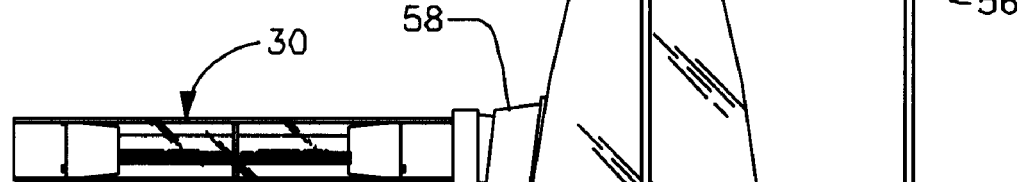
FIG. 18B is a side elevational view depicting the novel flexible, inflatable bag when at least partially inflated.
Figure 18C:
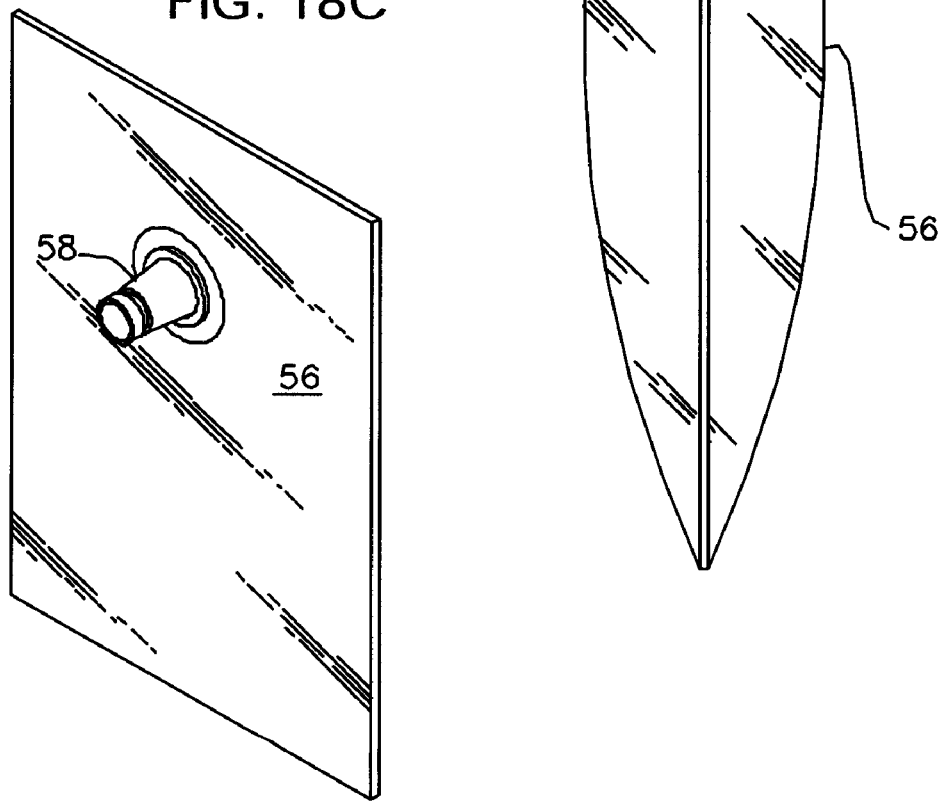
FIG. 18C is a perspective view of the flexible, inflatable bag depicted in FIGS. 18A and 18B.

The ninth embodiment, depicted in FIGS. 18A, 18B, and 18C, provides a flexible, inflatable bag 56 secured at nozzle 58 to the exit or discharge end of detector 30 in fluid communication with the lumen thereof. Bag 56 also defeats the intentions of a user who tries to blow past housing 12 and not through its lumen because flexible, inflatable bag 56 is at least slightly filled as depicted in FIG. 18B when air passes through said lumen. Bag 56 also facilitates measurement of the length of time that the user has exhaled through said lumen. For example, if it takes five (5) seconds to fill bag 56, it should be quite obvious if a user has blown into the bag for an ineffective time of just a second or so. Most indicator reagents will detect a substance and change color in about two seconds so a half-filled bag, in such a case, would indicate that the user has blown into detector 30 for at least the minimum amount of time. FIG. 18C provides a perspective view of said flexible, inflatable bag when it is not connected to detector 30.

Bag 56 may also be squeezed after use to empty its contents so that the user may be immediately re-tested.

FIGS. 19A and 19B provide an exploded and assembled view, respectively, of a container 60 that makes detector 30 truly portable. Main body 62 of container 60 is formed of a high impact plastic, as is closure means 64. Main body 62 has a closed end and an open end that is selectively closed by said closure means 64. In this way, container 60 protects detector 30 from breakage even if container 60 with detector 30 therewithin is carried in a pocket or other transport means that subjects container 60 to repeated blows of the type that could break detector 30 were it not protectively housed.

Advantageously, when provided in the form of a key fob connected to key ring 66 as depicted, container 60 is attractive and will always be carried by its user since keys are always carried. It is a simple matter to replace detector 30 after use, i.e., container 60 need not be repurchased when a new detector 30 is purchased.

Detector 30 is preferably wrapped by a paper instruction sheet and said instruction sheet is wrapped in a thin, flexible sheet of plastic 68, also known as a polybag. Plastic 68 maintains detector 30 in a sterile condition and also serves to snugly pack detector 30 within the hollow interior of main body 62, as best understood in connection with FIG. 19*b*, to provide still further protection against unintentional breakage of said detector during transport.

Nor is container 60 restricted in size so that it holds but one detector 30. As indicated in FIG. 20, container 60 may be sized to receive two, three, or more detectors.

Container 60, without regard to its size, may be covered with a light-reflective material to make it easy to see in low light conditions. It may also be covered with phosphorescent or luminescent materials so that it glows in the dark. It may also be provided in bright colors. A container may also include all of such features or any two of them.

However, detector 30 may also be sold as depicted in FIG. 21, i.e., without any container 60. This is the preferred method of packaging when re-fills are being sold. Thus, after a detector 30 is taken from a container 60 and used, the user need not re-purchase container 60 just to get another detector 30. Instead, detector 30 is sold as depicted in FIG. 21, with the paper instruction sheet and polybag 68 being in a flat, unrolled configuration. Polybag 68 is depicted with three (3) detectors therein, but it could contain only one (1) or two (2) detectors as well. A larger polybag could hold more than three (3) detectors 30.

The improved detection devices in accordance with this invention can be used to detect predetermined chemical concentrations of indicated substances in both liquid and gaseous body fluids. The indicator material can include more than one substance and can be contained in a single capsule or within separate capsules. The housings that form the test chamber may be pre-manufactured single disposable units or can be a part of a kit that allows for different sealed rupturable ampoules of indicator reagent to be insertable into housing 12 to test for different types of substances to detect the presence of legal or illegal drugs. Tests could also be conducted for halitosis, diabetes, or other medical condition that produces a tell-tale odor.

Likewise, housing 12 must provide a test chamber of structural integrity when subjected to the reagent(s), sample fluid and any interaction of the two. Thus, the housing must be substantially impermeable to and insoluble in such substances, as well as substantially impermeable to ambient environment. Vinyl is the preferred material for said housing.

However, any deformable substance that allows sufficient pressure or force to be applied through the wall of the housing to fracture ampoule 14 while having sufficient thickness and resistivity to avoid being punctured by random pressures from outside the housing as well as from glass fragments from the ruptured vessel is acceptable.

In a preferred embodiment, housing 12 is formed from a material such as polyvinyl chloride, a neoprene, polyester, or other inert, translucent flexible material that can be shaped into tubing of desired diameter. An exemplary tubing has a diameter of approximately 3/8" and is relatively thin-walled, i.e., in the range of from 1/32" to 1/64" thickness. The tubing may be flared at the entry end to form a funnel for urine and other liquid test fluids.

The material from which ampoule 14 is formed is substantially inert to and insoluble in the test fluid, reagent(s) and the ambient environment. Ampoule 14 must be capable of containing a solid, liquid or gaseous reagent and is preferably of thin-walled, easily rupturable construction. Suitable materials include glass, plastic and the like.

Ampoule 14 may also be segmented or compartmentalized through the use of dividers, or some other means to separate plural reagents from one another. The dividers may be porous or non-porous. When plural reagents are used, one of them may be dedicated to the detection of alcohol, one of them may be dedicated to the detection of marijuana, one may be dedicated to the detection of cocaine, and so on.

There may also be plural ampoules within a single housing, where each ampoule includes a different indicator reagent dedicated to detection of a different substance. The user must rupture all of the ampoules before using a detector of that type.

Ampoule 14 is thin-walled and may be formed of glass that has been slightly scored at or near the center. A relatively small pressure at the central area of housing 12 is therefore sufficient to rupture the walls of ampoule 14 without shattering it.

In an unillustrated embodiment, ampoule 14 has an open end upon which a membrane is mechanically placed by the ampoule manufacturer. Such ampoules have utility for housing heat-sensitive reagents.

The reagents which serve as the indicator material can be doped on a substrate or permeated into a porous substrate for release in the presence of a second solvent. It will be apparent to the skilled artisan that a number of permutations and combinations of reagents, solvents, substrates and the like can be configured proximate the test chamber in one or more vessels for single or sequential release to provide an integral, self-contained, disposable unit having a myriad of applications.

A thirteenth and fourteenth illustrative embodiment are depicted in FIG. 22. Note the absence of any ampoule 14 in these embodiments. The opposite ends of housing 12 are hermetically sealed by seals 70, 72 having respective pull tabs 70*a*, 70*b*. The seals are removed by pulling on said pull tabs when detector 30 is to be used. Indicator reagent 20 is contained between filters 16*a* and 18*a*. Thus, housing 12 need not be formed of a flexible and resilient material because said housing is not squeezed prior to use. The user merely removes seals 70, 72 and blows through the lumen of the housing. The indicator reagent changes color upon detection of a preselected substance just as in the above-described embodiments. Such thirteenth embodiment may also incorporate the streamers, the bag, the labels, and other elements of the first-described embodiments.

The fourteenth embodiment has the same structure as the thirteenth, but filters 16*a* and 18*a* are impregnated, coated, or otherwise treated with indicator reagents that differ from indicator reagent 20 positioned therebetween. For example, said filters could be treated with an indicator that changes color upon detection of cocaine. Thus, the breath of an inebriated cocaine user blowing into the lumen of detector 30 would activate both indicator reagents substantially simultaneously. Moreover, the filters could be treated with different indicator reagents so that the breath of an inebriated cocaine and marijuana user would substantially simultaneously activate all three of the indicator reagents.

A legend would be provided on the label as in the earlier embodiments to indicate what each color change indicates. Thus, although the structure of a FIG. 22 embodiment could include as many as three different indicator reagents, all reagents would operate independently of one another so a corporation interested only in marijuana testing, for example, could still purchase such embodiment.

It should also be observed that the indicator reagent could take forms other than powder or grain. For some tests, litmus paper could be provided in lieu of powder 20.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

The invention claimed is:

1. A disposable device for detecting the presence of a substance in a test fluid, comprising:
   a flexible and resilient first housing of generally cylindrical shape;
   an ampoule positioned within a lumen of said first housing;
   said ampoule adapted to sealably retain an indicator reagent;
   said ampoule adapted to be ruptured when subjected to a manually applied, radially inwardly directed force applied to said first housing;
   said ampoule having an outer diameter substantially less than a diameter of said lumen;
   a first filter positioned within a lumen of said first housing in abutting relation to a first end of said ampoule;
   a second filter positioned within a lumen of said first housing in abutting relation to a second end of said ampoule;
   said first and second filters being snugly received within said lumen of said first housing;
   said ampoule having rounded opposite ends;
   a first concavity formed in an inboard end of said first filter;
   a second concavity formed in an inboard end of said second filter;
   said first concavity being complementary in size and shape to a convex first rounded end of said ampoule;
   said second concavity being complementary in size and shape to a convex second rounded end of said ampoule;
   whereby said indicator reagent undergoes a visually detectible change in the presence of a predetermined amount of said substance;
   whereby said first and second concavities hold said ampoule in substantially coincident relation to a longitudinal axis of symmetry of said first housing.

2. The detector of claim 1, further comprising:
   each filter of said first and second filters having an outboard end of circular configuration in transverse cross section to provide said snug fit;
   each filter of said first and second filters having a downwardly tapered, diameter-reducing inboard end to facilitate sliding introduction of said first and second filters into opposite ends of said first housing.

3. The detector of claim 1, further comprising:
   said indicator reagent occupying about one-half of said ampoule by volume.

4. The detector of claim 1, further comprising:
   a first detent formed in said first housing in outboard relation to said first filter; and
   a second detent formed in said first housing in outboard relation to said second filter;
   whereby said first and second filters are constrained against longitudinal travel in an inboard direction by said ampoule and are constrained against longitudinal travel in an outboard direction by said first and second detents.

5. The detector of claim 1, further comprising:
   a compressible washer means having a central aperture;
   said compressible washer means being positioned about mid-length of said ampoule, said ampoule being received within said central aperture;
   said compressible washer means having an outer periphery in substantial contact with an inner wall of said first housing;
   said compressible washer having a radial extent from said central aperture to an outer periphery of said compressible washer that fully occupies a radial space between said first housing and said ampoule;
   whereby said manually applied radially inwardly directed force is applied to said compressible washer and causes compression of said central aperture and hence rupturing of said ampoule; and
   whereby said compressible washer provides a spacing between said first housing and said ampoule to reduce the chances that a glass shard from said ruptured ampoule will cut through said first housing and cut a finger or thumb of an individual applying said manual pressure.

6. The detector of claim 1, further comprising:
   a flexible and resilient second housing that ensleeves said first housing;
   whereby chances that glass shards, created by a ruptured ampoule in response to application of said manually applied radially-inwardly directed pressure against said first and second housings, will cut a finger or thumb of an individual applying said manual pressure is reduced by the presence of said second housing.

7. The detector of claim 1, further comprising:
   a first hingedly mounted flap formed in an outboard end of said first filter;
   said first flap adapted to admit fluid flow in one direction only;
   a second hingedly mounted flap formed in an outboard end of said second filter;
   said second flap adapted to admit fluid flow in one direction only;
   whereby a fluid may flow through said device in only one direction so that said indicator reagent cannot be inhaled; and
   whereby displacement of said first and second flaps indicates that a gaseous fluid is flowing through said detector, thereby defeating attempts of a user to defeat the detector by blowing around it.

8. The detector of claim 1, further comprising:
   a label having a first end that wraps completely around a first end of said housing;
   said label having a second end that wraps completely around a second end of said housing;

said label having a middle section that wraps partially around said housing;

whereby a window is created in said middle section;

whereby said window enhances visual inspection of said indicator reagent.

9. The detector of claim 8, further comprising:

said label having a front surface and a rear surface;

said front surface including instructional text thereon.

10. The detector of claim 8, further comprising:

said front surface including a color code that indicates what level of a substance has been detected when said indicator reagent changes to a color associated with a color on said color code.

11. The detector of claim 8, further comprising:

said rear surface of said label having a preselected color that contrasts with said indicator reagent when said indicator reagent has changed color;

whereby said rear surface is visible through said window when said indicator reagent is being visually inspected.

12. The detector of claim 1, further comprising:

said ampoule adapted to contain an indicator reagent that changes into a plurality of differing colors depending upon a percentage of said substance detected in said fluid;

a label secured to said housing;

a first plurality of color codes imprinted upon said label, each color code indicating a percentage of said substance present in said fluid;

whereby if said indicator reagent changes color in response to contact with said fluid, visual inspection of said plurality of color codes will indicate the percentage of said substance detected in said fluid.

13. The detector of claim 1, further comprising:

text imprinted directly on said first housing.

14. The detector of claim 1, further comprising:

graphical images imprinted directly on said first housing.

15. The detector of claim 1, further comprising:

at least one color code imprinted directly on said first housing.

16. The detector of claim 1, further comprising:

an elongate, flexible streamer secured to a preselected end of said housing;

said preselected end being a discharge end of said housing;

said streamer being mounted so that it is in fluid communication with fluid flowing through a lumen of said housing;

whereby said streamer remains substantially in a position of repose if fluid is not flowing through said housing;

whereby said streamer is displaced from said position of repose when fluid is flowing through said lumen;

whereby an amount of time that fluid flows through said lumen may be measured by measuring the amount of time said streamer is displaced from said position of repose.

17. The detector of claim 1, further comprising:

an inflatable, flexible bag secured to a discharge end of said first housing;

said inflatable, flexible bag being mounted so that it is in fluid communication with fluid flowing through said lumen of said first housing;

whereby said inflatable, flexible bag remains substantially in a position of repose if fluid is not flowing through said first housing;

whereby said inflatable, flexible bag is at least partially filled when fluid is flowing through said lumen.

18. The detector of claim 1, further comprising:

a container for housing said detector;

said container being formed of a material that is not easily deformed by external forces applied thereagainst;

whereby said detector may be transported when in said container and protected from breakage during said transport by said container.

19. The detector of claim 18, further comprising:

said container being provided in the form of a key fob so that said container and any keys used by a user of said detector will be connected to one another.

20. The detector of claim 18, further comprising:

said container including a main body sized to accommodate at least one detector;

said main body having a first closed end and a second open end;

a closure means for selectively closing said second open end;

whereby said at least one detector is fully enclosed within said main body when said at least one detector is positioned therewithin and said closure means is releasably secured to said second open end.

21. The detector of claim 4, further comprising:

a punch tool for forming said detents.

22. The detector of claim 1, further comprising:

said ampoule being weakened at a preselected rupture point.

23. The detector of claim 22, further comprising:

said ampoule being weakened at said preselected rupture point by a scoring line.

24. The detector of claim 18, further comprising:

an instruction sheet wrapped about said first housing;

a flexible sheet of plastic wrapped about said instruction sheet and said first housing;

said flexible sheet of plastic maintaining said first housing in a sterile condition; and said flexible sheet of plastic providing a packing material that cushions said first housing when said first housing is disposed within said container.

25. The detector of claim 21, further comprising:

a light-reflective material applied to said container to make said container easy to see in low-light conditions.

26. The detector of claim 22, further comprising:

said light-reflective material being selected from a group of light-reflective materials including phosphorescent materials, luminescent materials, and bright colors.

27. The detector of claim 1, further comprising:

said first housing being formed of a flexible, inert material selected from a group of materials including polyvinylchloride, polyester, and neoprene.

28. The detector of claim 1, further comprising:

said ampoule being thin-walled and being formed of an easily ruptured material that is inert and insoluble in the indicator reagent, in the test fluid, and in the ambient environment.

29. The detector of claim 1, further comprising:

said ampoule having at least one divider formed therein to divide it into at least two compartments;

there being a different indicator reagent positioned within each compartment so that the presence of at least two substances may be detected during a single use of said detector.

30. The detector of claim 1, further comprising:

at least a second ampoule positioned within said lumen of said first housing;

said at least a second ampoule containing a second indicator reagent therewithin;

whereby said ampoule and said at least a second ampoule must be ruptured prior to use of said detector.

31. The detector of claim 1, further comprising:

said ampoule having an open end;

a membrane disposed over said closing end in closing relation thereto;

said ampoule having utility for housing a heat-sensitive indicator reagent.

32. The detector of claim 1, further comprising:

said indicator reagent being doped on a substrate for release in the presence of a solvent.

33. The detector of claim 1, further comprising:

said indicator reagent being permeated into a porous substrate for release in the presence of a solvent.

34. The detector of claim 1, further comprising:

said indicator reagent having a form selected from a group of forms including grain, powder, and litmus paper.

\* \* \* \* \*